United States Patent [19]
Müller et al.

[11] Patent Number: 5,902,602
[45] Date of Patent: May 11, 1999

[54] ESTRADIOL-TTS HAVING WATER-BINDING ADDITIVES

[75] Inventors: Walter Müller; Michael Horstmann, both of Neuwied, Germany

[73] Assignee: LTS Lohmann Therapie-Systeme GmbH, Neuwied, Germany

[21] Appl. No.: 08/632,490
[22] PCT Filed: Aug. 12, 1995
[86] PCT No.: PCT/EP95/03201
§ 371 Date: Jun. 7, 1996
§ 102(e) Date: Jun. 7, 1996
[87] PCT Pub. No.: WO96/05814
PCT Pub. Date: Feb. 29, 1996

[30] Foreign Application Priority Data

Aug. 20, 1994 [DE] Germany .......................... 44 29 667

[51] Int. Cl.⁶ .............................. A61F 13/02; A61L 15/16
[52] U.S. Cl. .................... 424/449; 424/443; 424/446; 424/447; 424/448; 514/943; 514/946; 514/947
[58] Field of Search .................... 424/443, 446, 424/447, 448, 449; 514/943, 946, 947

[56] References Cited

U.S. PATENT DOCUMENTS

| | | | |
|---|---|---|---|
| 4,764,379 | 8/1988 | Sanders et al. | 424/449 |
| 4,788,062 | 11/1988 | Gale et al. | 424/449 |
| 4,816,258 | 3/1989 | Nedberger et al. | 424/448 |
| 4,863,738 | 9/1989 | Taskovich | 424/449 |
| 5,518,734 | 5/1996 | Stephano et al. | 424/448 |

FOREIGN PATENT DOCUMENTS

| | | |
|---|---|---|
| 0 421 454 | 4/1991 | European Pat. Off. . |
| 4 223 360 | 4/1993 | Germany . |
| 4 237 453 | 8/1993 | Germany . |

OTHER PUBLICATIONS

Higuchi, "Physical Chemical Analysis of Percutaneous Absorption Process From Creams and Ointments", J. Soc. Cosmetic Chem., 11, pp. 85–97 (1990).

Brusetta, "Structure Cristalline et Moleculaire de l'Oestradiol Hemihydrate", Acta Cryst. (1972) B28, pp. 560–567.

Kuhnert–Brandstätter et al., "Thermoanalytische und IR–spektroskopische Untersuchungen an verschiedenen Kristallformen von Arzneistoffen aus der Ostradiol–und Androstangruppe" Scientia Pharmaceutica, 44 (3), 1976, pp. 177–190.

*Primary Examiner*—Thurman K. Page
*Assistant Examiner*—Kathryne E. Shelborne
*Attorney, Agent, or Firm*—Wenderoth, Lind & Ponack, L.L.P.

[57] ABSTRACT

A transdermal therapeutic system comprising the active substance estradiol and having a layered structure of a backing layer which is impermeable to active substances and moisture, and active substance-containing matrix, and, if necessary, a removable protective layer covering the matrix, is characterized by the fact that the matrix comprises glycerol either comprising a maximum of 1%-wt. of water or being substantially free from water.

19 Claims, No Drawings

ESTRADIOL-TTS HAVING WATER-BINDING ADDITIVES

The present invention relates to a transdermal therapeutic system comprising the active substance estradiol and having a layered structure of a backing layer which is impermeable to active substances and moisture, an active substance-containing matrix, and, if necessary, a removable protective layer covering the matrix.

BACKGROUND OF THE INVENTION

In the therapy of several diseases, Transdermal Therapeutic Systems (TTS) have been introduced on the market for some time now.

Also, TTSs comprising the active substance estradiol have been on the market as therapeutic agents for climacteric complaints, and, since a short time ago, also against osteoporosis; they have proved successful in therapy.

In the following the term "estradiol" is to be understood as the anhydrous substance of 17-β-estradiol.

A disadvantage of prior art systems is the insufficient capability of the active substance to permeate through the skin. This cannot be increased beyond a certain limit, the so-called "saturation flow", although several galenic measures with respect to the TTS-design have been taken (use of multilayer systems, use of controlling membranes, variation of the active substance concentration, modification of the base polymer, and the like). This finding that the transdermal flow of an active substance from the solid, finely dispersed phase cannot be increased further in principle, can already be found in the still trailblazing works of Higuchi (e.g., T. Higuchi; Physical Chemical Analysis of percutaneous absorption process from creams and ointments. J. Soc. Cosmetic Chem. 11, p. 85–97 (1990).

The systems described in EP 0 421 454 comprise estradiol in an acrylic polymer under addition of "crystallization inhibitors" and tackifying resins. Swelling agents are contained to give protection against premature loss of adhesive force.

In addition, with a lot of active substances, so-called "enhancers" can be added to the TTS during production. These are usually liquid admixtures improving the absorption properties of human skin; for this reason, they allow the absorption of the active substance from a sufficiently small TTS-surface.

Readily volatile enhancers, e.g., ethanol used for the active substance estradiol, particularly involve problems caused by an extreme softening of the TTSs' adhesive layers, and they require additional bulky compartments in the system, rendering the TTS unacceptably thick.

The addition of less volatile, however, mostly less active enhancers (e.g., glycerol esters, cyclic amides, eucalyptol) allows the production of matrix systems comprising active substances and an absorption-promoting component in one or several layers. However, the insufficient adhesive force of these TTSs is disadvantageous. U.S. Pat. No. 4 863 738 represents one of many examples claiming the application of active substances, e.g., estradiol, together with a certain enhancer (in this case glycerol monooleate) in an optional TTS-matrix and in an optional concentration.

However, even such a prior art TTS does not permit a satisfactory therapy either. The reason is that either the chosen enhancers are poorly tolerated by the skin or that the systems have unacceptably large surfaces owing to the still insufficient flow through the skin.

Another (theoretic) possibility of increasing the active substance flow through the skin is to dissolve more active substance molecularly disperse, i.e., crystal-free, in the TTS than corresponds to the saturation solubility. The permeation rate through the skin increases to the same extent as the degree of supersaturation of these systems. However, these physical states are thermodynamically unstable, therefore these forms of administration are not storable. Within some months or years, at the latest, a spontaneous unforeseeable precipitation of active substance will take place so that the flow rate through the skin gradually decreases to the saturation flow level; depending on the starting concentration, this results in losing a great portion of the initial therapeutic activity.

This process occurring during storage is due to particular physicochemical characteristic features of estradiol.

At room temperature and normal relative air humidity (20–60% relative humidity), estradiol is not present in one of the two known anhydric modifications (I and II) but as a semihydrate (Busetta, Acta Cryst. 1972, B28, 560). Owing to the layered structure stabilized via hydrogen bridges, and because of the diffusional compactness of the crystal compound, the hydrate can be subjected to a short-term heat treatment to temperatures of about 170° C. without decomposition thereof (Kuhnert-Brandstätter and Winkler (1976) Scientia Pharmaceutica 44 (3), 177–190). However, estradiol-semihydrate can quantitatively be converted into the anhydrous form already at about 120° C. by way of enlarging the crystal surface by means of micronizing. According to the inventors' observations, the transformation already takes place at about 90° C. if heating is conducted slowly (0.2–1 K/min) and in case of a particularly fine substance.

With decreasing partial water vapor pressure, on the other hand, estradiol has a higher solubility in some polymers, particularly in polyacrylates. According to Fick's law, higher concentrations with otherwise same conditions increase the diffusion flow through the skin; for this reason such a concentration increase is very desirable in transdermal therapeutic systems. However, the water introduced with the estradiol-semihydrate is already sufficient to cause gradual recrystallization from the solution as estradiol-semihydrate (Kuhnert-Brandstätter and Winkler (1976) Scientia Pharmaceutica 44 (3), 177–190). During crystallization, the flow rate from the system to the skin considerably decreases with the diminishing concentration.

Accordingly, transdermal therapeutic systems are known that offer a pharmacotherapeutically satisfying solution by exactly regulating the concentration to below the saturation solubility of the estradiol-anhydrate (DE-PS 42 37 453) or by using partially undissolved, disperse estradiol-anhydrate (DE-PS 42 23 360). Even in consideration of this latest state of the art, it is important to maintain a sufficiently low atmospheric humidity during production and storage of an estradiol-TTS in order to avoid large-area precipitation of the poorly soluble estradiol-semihydrate.

To this end, a package having a low water-vapor permeability can be used in principle. However, owing to the small estradiol amounts contained in today's TTSs, very small amounts of humidity are sufficient to cause precipitation of the estradiol-semihydrate. If, for example, 2 mg of estradiol (anhydrous) are present in a TTS in dissolved form, an amount (calculated on the basis of the molecular-weight ratios) of only 66.1 μg of water can cause complete precipitation. Using conventional packaging means, it is therefore very difficult to exclude entry of such small quantities of moisture over storage periods of several years.

DESCRIPTION OF THE INVENTION

Accordingly, it is the object of the present invention to provide a transdermal therapeutic system comprising estradiol, that comprises a long-term protection against precipitation of the estradiol-semihydrate, said protection being incorporated in the active substance-containing layers themselves, and which prevents crystallization to the estradiol-semihydrate.

Glycerol is a very polar compound and miscible with water in any ratio. Anhydrous glycerol is very hygroscopic and can be used as dehydrating agent under certain conditions. It can be demonstrated by way of experiments that its anhydrous form is able to remove crystal water from the estradiol-semihydrate. In this connection, the term "anhydrous" or "substantially anhydrous or substantially free from water" is to be understood as a water content of less than 1%. If estradiof-semihydrate is stirred in anhydrous glycerol at room temperature for about 24 hours, the flat-shaped crystals of the semihydrate are converted into thin needles. These needles are either the anhydrous estradiol or an estradiol-glycerol-solvate. An addition of only 2% of water to the glycerol used for this test prevents this reaction. This clearly demonstrates that the species resulting during the reaction with anhydrous glycerol does not comprise any water.

The above-mentioned embodiment of a TTS according to the present invention can be realized in different manners. The most simple form is a single-layer matrix system whose matrix simultaneously has a pressure-sensitive adhesive function, rendering a special adhesive layer superfluous. The glycerol dispersed in the matrix ensures an equilibrium-moisture content over the storage period that is low enough to render precipitation of the estradiol-semihydrate impossible.

If the adhesive force of this layer is insufficient or if direct skin contact of this layer is to be avoided, the matrix may be laminated with a special skin adhesive layer.

If a membrane which is hardly permeable to estradiol is introduced between such a matrix, which comprises estradiol and water-binding disperse glycerol, and the adhesive layer, an active substance release is achieved which is controlled by the patch rather than by the skin.

In addition to the wide-spread acrylic acid copolymers suitable for the use with estradiol, other polymers may also be used as base material, such as polyisobutylene, polyvinyl acetate and copolymers, synthetic rubber, block polymers of styrene and isoprene or of styrene and butadiene, and silicones.

In any case, the characterizing feature of transdermal therapeutic systems according to the present invention is the presence of disperse, substantially anhydrous glycerol. In this connection, the exact amount of glycerol in the system must be chosen such that, on the one hand, the solubility of glycerol in the system is exceeded and that it is present as separate phase dispersed in small droplets, and, on the other hand, that the total moisture-binding capacity in the system is sufficient. An addition in the range of 2 or even 1 percent may be considered as minimum amount; the upper limit is determined by mechanical values, such as flowability of the matrix, adhesive force, and processibility. In general, a proportion of 10 to 50 percent by weight, preferably between 10 and 35 percent by weight is desired.

EXAMPLES

Example 1

2.0 g of 17-β-estradiol-semihydrate, micronized is mixed with 2.75 g of anhydrous glycerol, 25 g of an acrylic ester copolymer solution (solids content 42%) and 5.9 g of colophony-glycerol ester derivative (Staybelite Ester 5E, of Hercules)

and subsequently coated on a 100 μm siliconized polyester film in such a manner that the coating weight amounts to 120 g/m$^2$.

The coating is dried at.25° C., at 50° C., at 80° C. and at 95° C., each time for 10 minutes. A 10 μm polyester film is immediately applied (laminated) on the dry layer under roller pressure, avoiding the formation of air bubbles.

Transdermal systems of 16 cm$^2$ are obtained by punching using a wad punch. These are immediately packed into moistureproof, heat-sealable bags.

Example 2

2.0 g of 17-β-estradiol-semihydrate, micronized, 60.0 g of Cariflex TR 1107® (styrene-isoprene block polymer), 120.0 g of Staybelite Ester 5E (thermoplastic ester gum of colophony derivatives), 50.0 g of viscous paraffin 50.0 g of anhydrous glycerol are rendered molten in an evacuatable kneader at 130° C. and brought into an externally homogeneous form by means of kneading within ten hours.

The melt is cooled down to 120° C.; in a continuous coating line it is subsequently coated onto a siliconized polyester film of 1 00 μm thickness in such a manner that the weight per unit area amounts to 200 g/m$^2$.

Afterwards a polyester film 15 μm thick is applied (laminated) under roll pressure on the still hot layer, avoiding the formation of air bubbles.

Transdermal systems of 16 cm$^2$ are obtained by punching using a wad punch.

We claim:

1. A storage stable transdermal therapeutic system comprising the active substance estradiol and having a layered structure of a backing layer which is impermeable to active substances and moisture, an active substance-containing matrix, wherein the matrix comprises at least 2% by weight of glycerol that has a maximum of 1%-wt. of water or is substantially free from water, said amount of said glycerol providing protection against precipitation of estriol semihydrate during storage.

2. A transdermal therapeutic system according to claim 1, wherein the matrix consists of several layers at least one layer comprising glycerol that has a maximum of 1%-wt. of water or is substantially free from water.

3. A transdermal therapeutic system according to claim 1, wherein the estradiol contained in the matrix is present as a dispersion of an anhydrous crystallizate.

4. A transdermal therapeutic system according to claim 1, wherein the base material of the matrix or of one of its layers is an acrylic-acid ester copolymer.

5. A transdermal therapeutic system according to claim 4, wherein the acrylic-acid ester copolymer has a solubility for the crystallizate of the estradiol of between 0.4 and 3.0%.

6. A process for the production of a transdermal therapeutic system according to claim 1 which comprises:

a) preparing a suspension of estradiol-semihydrate and water-binding glycerol in a solution, dispersion, or melt of the matrix base material, b) coating a carrier foil with the suspension, and c) drying the applied layer by heating to 50 to 175° C. to convert estradiol-semihydrate into anhydrous estradiol.

7. A process according to claim 6, wherein the resulting transdermal therapeutic system is packed into a packaging means which can be sealed in a gas-tight manner and that a desiccant is additionally added to said package.

8. A transdermal therapeutic system according to claim 1, which contains in addition a removable protective layer covering the matrix.

9. A transdermal therapeutic system according to claim 1, wherein the matrix comprises between 10 and 50% by weight of glycerol that has a maximum of 1% wt, of water or is substantially free from water.

10. A transdermal therapeutic system according to claim 9, wherein the amount of glycerol is in the range from 10 to 35% by weight.

11. A storage stable transdermal therapeutic system comprising the active substance estradiol and having a layered structure of a backing layer which is impermeable to active substances and moisture, an active substance-containing matrix, wherein the matrix contains at least 2% by weight of glycerol in disperse form that has a maximum of 1%-wt. of water or is substantially free from water.

12. A transdermal therapeutic system according to claim 11, wherein the amount of glycerol exceeds its solubility in the system and the glycerol is present as a separate phase dispersed in small droplets therein.

13. A transdermal therapeutic system according to claim 11, wherein the matrix consists of several layers at least one layer comprising glycerol that has a maximum of 1%-wt. of water or is substantially free from water.

14. A transdermal therapeutic system according to claim 11, wherein the estradiol contained in the matrix is present as a dispersion of an anhydrous crystallizate.

15. A transdermal therapeutic system according to claim 11, wherein the base material of the matrix or of one of its layers is an acrylic-acid ester copolymer.

16. A transdermal therapeutic system according to claim 15, wherein the acrylic-acid ester copolymer has a solubility for the crystallizate of the estradiol of between 0.4 and 3.0%.

17. A transdermal therapeutic system according to claim 11, which contains in addition a removable protective layer covering the matrix.

18. A transdermal therapeutic system according to claim 11, wherein the matrix comprises between 10 and 50% by weight of glycerol that has a maximum of 1%-wt. of water or is substantially free from water.

19. A transdermal therapeutic system according to claim 18, wherein the amount of glycerol is in the range from 10 to 35% by weight.

* * * * *